United States Patent [19]

Findeisen et al.

[11] Patent Number: 5,441,924

[45] Date of Patent: Aug. 15, 1995

[54] HERBICIDAL SUBSTITUTED TRIAZOLINONES

[75] Inventors: Kurt Findeisen; Hans-Joachim Santel, both of Leverkusen; Klaus Lürssen; Robert R. Schmidt, both of Bergisch-Gladbach, all of Germany

[73] Assignee: Bayer Aktiengesellschaft, Leverkusen, Germany

[21] Appl. No.: 316,198

[22] Filed: Sep. 30, 1994

Related U.S. Application Data

[60] Continuation of Ser. No. 28,469, Mar. 9, 1993, abandoned, which is a division of Ser. No. 852,482, Mar. 16, 1992, Pat. No. 5,238,902, which is a continuation of Ser. No. 606,394, Oct. 31, 1990, abandoned.

[30] Foreign Application Priority Data

Dec. 9, 1989 [DE] Germany .................. 39 39 952.4

[51] Int. Cl.⁶ ............... A01N 43/84; A01N 43/653; C07D 413/04; C07D 403/04
[52] U.S. Cl. ................... 504/225; 504/219; 504/235; 504/248; 504/273; 540/603; 544/132; 544/366; 546/210; 548/263.8
[58] Field of Search ........... 504/219, 225, 235, 248, 504/273; 540/603; 544/132, 366; 546/218; 548/263.8

[56] References Cited

U.S. PATENT DOCUMENTS

5,061,311  10/1991  Findeisen et al. .................. 71/92

FOREIGN PATENT DOCUMENTS

2042660  3/1972  Germany .................. 548/263.8

*Primary Examiner*—Patricia L. Morris
*Attorney, Agent, or Firm*—William C. Gerstenzang; Sprung Horn Kramer & Woods

[57] ABSTRACT

Substituted triazolinones of the formula

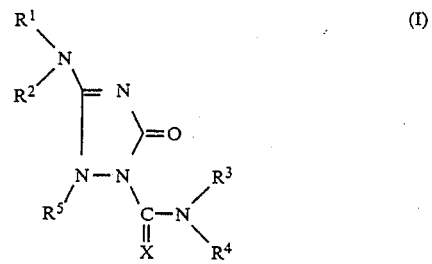

wherein $R^1$, $R^2$, $R^3$, $R^4$, $R^5$ and $X$ having the meanings defined in the specification, are useful as herbicides.

3 Claims, No Drawings

HERBICIDAL SUBSTITUTED TRIAZOLINONES

This application is a continuation of application Ser. No. 08/028,469, filed on Mar. 9, 1993, which is a division of application Ser. No. 07/852/482, filed Mar. 16, 1992, now U.S. Pat. No. 5,238,902, which is a continuation of application Ser. No. 07/606,394, filed Oct. 31, 1990, now abandoned.

The invention relates to novel substituted triazolinones, to a plurality of processes for their preparation and their use as herbicides.

Novel substituted triazolinones of the general formula (I) have been found

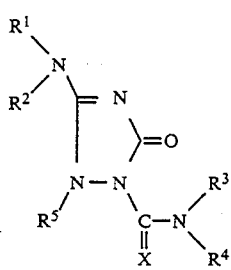

(I)

in which
$R^1$ and $R^2$ independently of one another, each represents alkyl, alkenyl, alkynyl, halogenoalkyl, halogenoalkenyl, halogenoalkynyl, cyanoalkyl, alkoxyalkyl, alkoxy, cycloalkyl, cycloalkylalkyl, aryl, aralkyl or heteroaryl, each of which is optionally substituted, or, together with the nitrogen atom to which they are bonded, represent an optionally substituted heterocycle, $R^3$ and $R^4$ independently of one another, each represents hydrogen, alkyl, alkenyl, alkynyl, halogenoalkyl, halogenoalkenyl, halogenoalkynyl, cyanoalkyl, hydroxyalkyl, alkoxyalkyl, alkylaminoalkyl, dialkylaminoalkyl, alkoxycarbonylalkyl or alkoxycarbonylalkenyl; cycloalkyl, cycloalkylalkyl, cycloalkenyl or cycloalkenylalkyl, each of which is optionally substituted; optionally substituted heterocyclylalkyl; aralkyl, aroyl or aryl, each of which is optionally substituted, alkoxy, alkenyloxy, alkynyloxy, aralkyloxy or aryloxy, or, together with the nitrogen to which they are bonded, represent an optionally substituted heterocycle, $R^5$ represents alkyl or cycloalkyl and X represents oxygen or sulphur.

Furthermore, it has been found that the novel substituted triazolinones of the general formula (I) are obtained if a) triazolinones of the general formula (II)

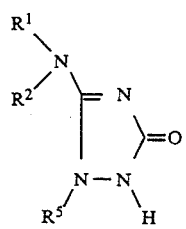

(II)

in which
$R^1$, $R^2$ and $R^5$ have the meanings given above, and/or tautomers of these compounds, i.e. the corresponding hydroxytriazoles, are reacted, optionally in the presence of a reaction auxiliary and optionally in the presence of a diluent, with iso(thio)cyanates of the general formula (III)

$$R^4-N=C=X \qquad (III)$$

in which
$R^4$ and X have the meanings given above, or if b) chlorocarbonyl-triazolinones of the general formula (IV)

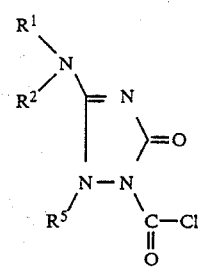

(IV)

in which
$R^1$, $R^2$ and $R^5$ have the meanings given above, are reacted, optionally in the presence of an acid-binder and optionally in the presence of a diluent, with amines of the general formula (V)

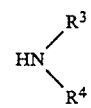

(V)

in which
$R^3$ and $R^4$ have the meanings given above.

Finally, it has been found that the novel substituted triazolinones of the general formula (I) have interesting herbicidal properties.

In the general formulae, halogen denotes fluorine, chlorine, bromine and iodine, preferably fluorine, chlorine or bromine, in particular fluorine or chlorine.

Optionally substituted aryl groups such as, for example, aryl, aralkyl and aryloxycan carry one or more, preferably 1 to 5, in particular 1 to 3, and particularly preferably 1 or 2, identical or different substituents.

In aryl-containing radicals, aryl preferably represents phenyl or naphthyl.

The radicals $R^1$ and $R^2$, or $R^3$ and $R^4$, in the event that they form a heterocycle together with the nitrogen atom to which they are bonded, preferably represent a heterocycle which is optionally mono-, di- or tri-substituted by identical or different substituents, and has the formula

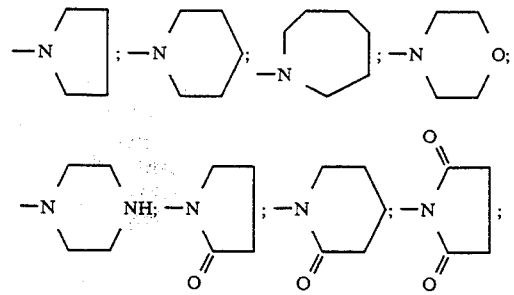

-continued

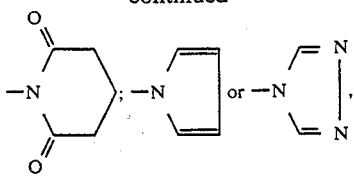

the selected substituents being:
halogen, and alkyl or halogenoalkyl, each of which is straight-chain or branched, and each having 1 to 4 carbon atoms and, if appropriate, 1 to 9, preferably 1 to 5, in particular 1 to 3, identical or different halogen atoms. Particular preference is given to the substituents methyl, ethyl, n- or i-propyl, chlorine and trifluoromethyl.

The heterocyclyl moiety in the meaning of heterocyclylalkyl for $R^3$ and $R^4$ preferably represents the following heterocycles:

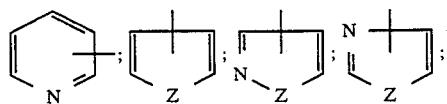

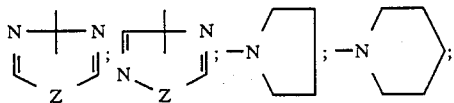

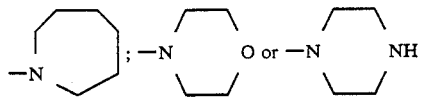

Z representing oxygen or sulphur in each case.

Alkyl in the meaning of heterocyclylalkyl represents for example methyl, ethyl, n- or iso-propyl, n-, iso-, sec- or tert-butyl.

The heterocycle in the meaning of heterocyclylalkyl can be mono- or poly-substituted, preferably mono- to tri-substituted, in particular mono- or di-substituted by identical or different alkyl or halogenoalkyl radicals, each of which may be straight-chain or branched, having 1 to 4, preferably 1 or 2 carbon atoms and 1 to 9, preferably 1 to 5, in particular 1 to 3, identical or different halogen atoms or by alkanediyl or alkenediyl, each of which is doubly linked, having up to 4 carbon atoms. In particular, the substituents selected are methyl and ethyl.

Preference is given to compounds of the formula (I) in which
$R^1$ and $R^2$, independently of one another, represent alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl each having 2 to 8 carbon atoms and 1 to 15 or 13 identical or different halogen atoms respectively, cyanoalkyl, alkoxyalkyl or alkoxy, each having 1 to 6 carbon atoms in the individual alkyl moieties, each of the preceding species being straight-chain or branched, represent cycloalkyl having 3 to 7 carbon atoms, represent cycloalkylalkyl having 3 to 7 carbon atoms in the cycloalkyl moiety and 1 to 6 carbon atoms in the alkyl moiety or represent aralkyl having 6 to 10 carbon atoms in the aryl moiety and 1 to 6 carbon atoms in the alkyl moiety, aryl having 6 to 10 carbon atoms or heteroaryl having 2 to 9 carbon atoms and 1 to 3 hetero atoms, in particular nitrogen, oxygen and/or sulphur, each of these species being optionally mono- or poly-substituted by identical or different substituents, suitable substituents in each case being: halogen, cyano, nitro and also alkyl, alkoxy, alkylthio, halogenoalkyl, halogenoalkoxy or halogenoalkylthio, each of which may be straight-chain or branched, each having 1 to 4 carbon atoms and, if appropriate, 1 to 9 identical or different halogen atoms or and $R^2$, together with the nitrogen atom to which they are bonded, represent a 5- to 10-membered heterocycle which is optionally mono- or poly-substituted by identical or different substituents and may optionally contain 1 to 2 other hetero atoms, in particular nitrogen, oxygen and/or sulphur, suitable substituents being: halogen and also alkyl or halogenoalkyl, each of which may be straight-chain or branched, each having 1 to 4 carbon atoms and, if appropriate, 1 to 9 identical or different halogen atoms and also 1 to 2 oxo or thioxo groups, $R^3$ and $R^4$, independently of one another, represent hydrogen, represent alkyl having 1 to 18 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl, each having 2 to 8 carbon atoms and 1 to 15 or 13 identical or different halogen atoms respectively, cyanoalkyl having 1 to 8 carbon atoms, hydroxyalkyl having 1 to 8 carbon atoms and 1 to 6 hydroxyl groups, alkoxyalkyl, alkoxycarbonylalkyl or alkoxycarbonylalkenyl, each having up to 6 carbon atoms in the individual alkyl or alkenyl moieties, alkylaminoalkyl or dialkylaminoalkyl, each having 1 to 6 carbon atoms in the individual alkyl moieties, each of these species being straight-chain or branched, or represent cycloalkyl, cycloalkylalkyl, cycloalkenyl or cycloalkenylalkyl, each having 3 to 8 carbon atoms in the cycloalbyl or cycloalkenyl moiety and, if appropriate, 1 to 6 carbon atoms in the alkyl moiety, each of which is optionally mono- or poly-substituted by identical or different substituents, suitable substituents in each case being: halogen, cyano and also alkyl or halogenoalkyl, each of which may be straight-chain or branched, each having 1 to 4 carbon atoms and, if appropriate, 1 to 9 identical or different halogen atoms or alkanediyl or alkenediyl, each of which is doubly linked, each having up to 4 carbon atoms; furthermore $R^3$ and $R^4$, independently of one another represent heterocyclylalkyl having 1 to 6 carbon atoms in the straight-chain or branched alkyl moiety and 1 to 9 carbon atoms and 1 to 3 hetero atoms in the heterocyclyl moiety, in particular nitrogen, oxygen, and/or sulphur, the heterocyclyl moiety being optionally mono- or poly-substituted by identical or different substituents, suitable substituents being: halogen, cyano, nitro and also alkyl, alkoxy, alkylthio, halogenoalkyl, halogenoalkoxy, halogenoalkylthio or alkoxycarbonyl, each of which is straight-chain or branched, each having 1 to 5 carbon atoms and, if appropriate, 1 to 9 identical or different halogen atoms; furthermore, R³ and R⁴, independently of one another, represent alkoxy having 1 to 8 carbon atoms, alkenyloxy having 2 to 8 carbon atoms or alkynyloxy having 2 to 8 carbon atoms, each being straight-chain or branched, or represent aralkyl, aralkyloxy, aryloxy, aroyl or aryl, each having 6 to 10 carbon atoms in the aryl moiety and, if appropriate, 1 to 6 carbon atoms in the alkyl moiety, each of which is optionally mono- or poly-substituted by identical or different substituents, suitable aryl substituents in each case being: halogen, cyano, nitro, hydroxyl and also alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which may be straight-chain or branched, each having 1 to 6 carbon atoms and, if appropriate, 1 to 9 identical or different halogen atoms, cycloalkyl having 3 to 6 carbon atoms or phenoxy and suitable alkyl substituents, if desired, being: halogen or cyano, or R³ and R⁴, together with the nitrogen atom to which they are bonded, represent a 5- to 10-membered heterocycle which is optionally mono- or poly-substituted by identical or different substituents and optionally contains 1 to 2 other hetero atoms, in particular nitrogen, oxygen and/or sulphur, suitable substituents being: halogen and also alkyl or halogenoalkyl, each of which may be straight-chain or branched, each having 1 to 4 carbon atoms and, if appropriate, 1 to 9 identical or different halogen atoms, and also 1 to 2 oxo or thioxo groups, R⁵ represents straight-chain or branched alkyl having 1 to 8 carbon atoms or cycloalkyl having 3 to 8 carbon atoms and X represents oxygen or sulphur.

Particular preference is given to the compounds of the formula (I) in which

R¹ and R² independently of one another, each represents methyl, ethyl, n- or i-propyl, n-, i-, s- or t-butyl, n- or i-pentyl, allyl, propargyl, represents halogenoalkyl having 1 to 4 carbon atoms, halogenoalkenyl having 3 to 6 carbon atoms or halogenoalkinyl having 3 to 6 carbon atoms and in each case having 1 to 9 identical or different halogen atoms, each of these species being straight-chain or branched, represents cyanoethyl, methoxymethyl, methoxyethyl, dimethoxyethyl, methoxy, ethoxy, represents cyclopropyl, cyclopropylmethyl, cyclopentyl, cyclohexyl, cyclohexylmethyl, cyclohexylethyl, cyclopentylmethyl or represents benzyl, phenylethyl or phenyl, each of which is optionally mono- to tri-substituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio or R¹ and R² together with the nitrogen atom to which they are bonded, represent a heterocycle of the formula

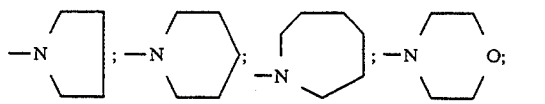

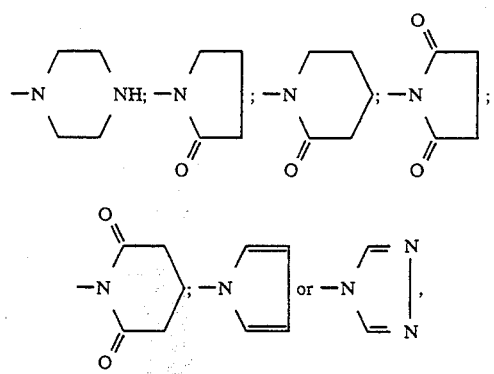

which is optionally mono- to tri-substituted by identical or different substituents, suitable substituents being: methyl, ethyl, n- or i-propyl, chloro or trifluoromethyl, R³ represents hydrogen or methyl, R⁴ represents methyl, ethyl, n- or i-propyl, n-, i-, s- or t-butyl, represents pentyl, hexyl, heptyl, octyl, nonyl, decyl or dodecyl, each of which is straight-chain or branched, represents allyl, represents butenyl, pentenyl, hexenyl, propargyl, butynyl, pentynyl or hexynyl, each of which is straight-chain or branched, represents straight-chain or branched halogenoalkyl having 1 to 6 carbon atoms and 1 to 9 identical or different halogen atoms, in particular fluorine, chlorine or bromine, represents halogenoalkenyl or halogenoalkynyl, each of which is straight-chain or branched, each having 3 to 5 carbon atoms and 1 to 3 halogen atoms, in particular fluorine or chlorine, represents cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl, each of which is straight-chain or branched, each having up to 4 carbon atoms in the individual alkyl and alkenyl moieties, or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, each of which is optionally mono- to tri-substituted by identical or different substituents, suitable substituents in each case being: fluorine, chlorine, bromine, methyl, ethyl, n- or i- propyl, n-, i-, s- or t-butyl, cyano, methanediyl, ethanediyl, butanediyl or butadienediyl; furthermore represents heterocyclylmethyl, heterocyclylpropyl or heterocyclylethyl, each of which is optionally mono- to tri-substituted by identical or different substituents in the heterocyclyl moiety, suitable heterocycles in each case being:

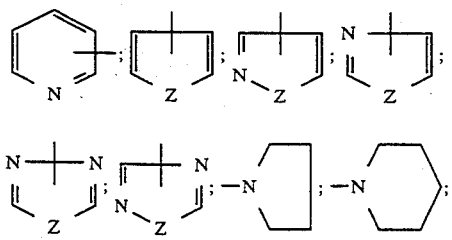

-continued

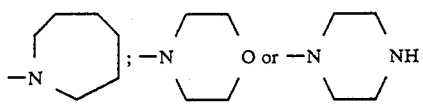

Z in each case representing oxygen or sulphur and suitable substituents being: fluorine, chlorine, bromine, cyano, nitro, methyl, ethyl, n- or i- propyl, n-, i-, s- or t-butyl, methoxy, ethoxy, methylthio, trifluoromethyl, trifluoromethoxy or trifluoromethylthio; $R^4$ furthermore represents alkoxy having 1 to 6 carbon atoms, alkenyloxy having 3 to 6 carbon atoms or alkynyloxy having 3 to 6 carbon atoms, each of which is straight-chain or branched, or represents bonzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, each of which is optionally straight-chain or branched and optionally mono- to tri-substituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy; or $R^3$ and $R^4$, together with the nitrogen atom to which they are bonded, represent a heterocycle of the formula

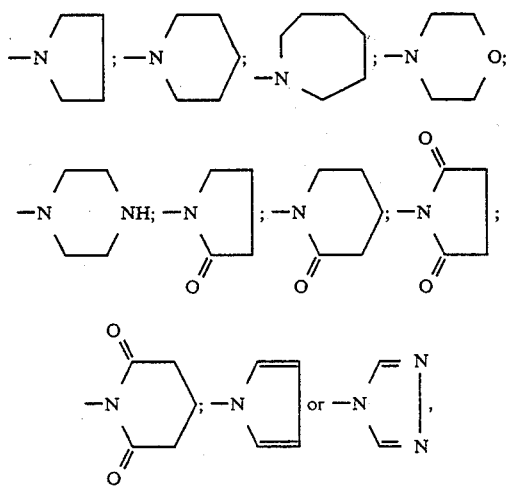

which is optionally mono- to tri-substituted by identical or different substituents, suitable substituents being: methyl, ethyl, n- or i-propyl, chlorine or trifluoromethyl, $R^5$ represents methyl, ethyl, propyl, isopropyl, n-, i-, s- or t-butyl, cyclopropyl, cyclobutyl, cyclopentyl or cyclohexyl and X represents oxygen or sulphur.

Most particular preference is given to the compounds of the formula (I) in which $R^1$ represents methyl, ethyl, n- or i-propyl, n-, i-, s- or t-butyl, n- or i-pentyl, cyclopropyl, cyclopentyl or cyclohexyl, $R^2$ represents methyl, ethyl, n- or i-propyl, n-, i-, s- or t-butyl, n- or i-pentyl or $R^1$ and $R^2$, together with the nitrogen atom to which they are bonded, represent a heterocycle of the formula

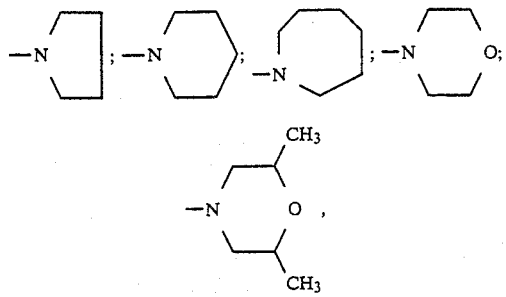

$R^3$ represents hydrogen, $R^4$ represents methyl, ethyl, n- or i-propyl, n-, i-, s- or t-butyl, allyl, propargyl, represents pentyl, hexyl, heptyl, butenyl, pentenyl, butynyl, pentyhyl or hexynyl, each of which is straight-chain or branched, halogenoalkyl having 1 to 5 carbon atoms and 1 to 9 identical or different halogen atoms, in particular fluorine or chlorine, cyclopropyl, cyclopentyl or cyclohexyl, each of which is optionally mono-, di- or tri-substituted by identical or different substituents from the series comprising methyl, ethyl, fluorine or chlorine, represents phenyl, benzyl or phenylethyl, each of which is optionally mono-, di- or tri-substituted, in particular monosubstituted, by identical or different substituents, the substituents chosen being fluorine, chlorine, methyl, ethyl, methoxy, ethoxy, methylthio, trifluoromethoxy and trifluoromethylthio, and benzyl or phenylethyl, in particular, being unsubstituted, $R^5$ represents methyl, ethyl, n- or i-propyl, in particular methyl, and X represents oxygen.

If, for example, the starting materials used are 5-dimethylamino-1-methyl-1,2-dihydro-3H-1,2,4-triazol-3-one and tert-butyl isocyanate, the course of the reaction of the process (a) according to the invention can be represented by the following reaction scheme:

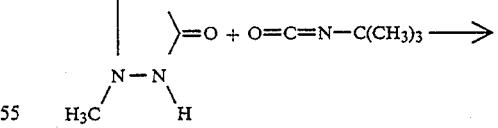

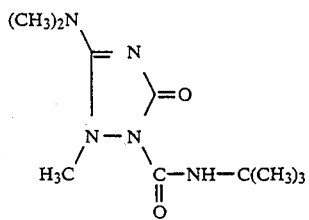

If, for example, the starting materials used are 2-chlorocarbonyl-1-methyl-5-piperidino-1,2-dihydro-3H-1,2,4-triazol-3-one and diethylamine, the course of the reaction of the process (b) according to the invention can be represented by the following reaction scheme:

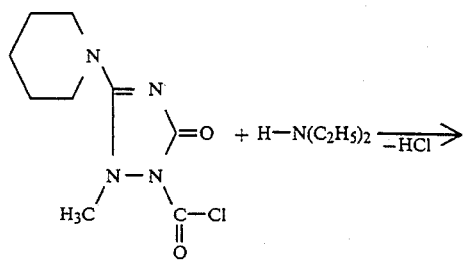

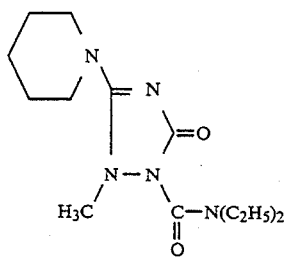

The radicals ($R^1$, $R^2$, X, etc.) which are defined in the active compounds of the formula (I) also have the meanings given in the compounds of the formula (I) in all definition contexts of the intermediates and precursors. This is also the case for the radicals which are repeatedly mentioned in the precursors and intermediates.

The starting materials of the formula (II) or the hydroxytriazoles tautomeric thereto are known and/or can be prepared by processes which are known per se (cf. DE-A-2,042,660, DE-A-2,330,089, DE-A-2,428,204 and DE-A2,537,973).

For example, the triazolinones of the formula (II) are obtained if cyanamides of the formula (VI)

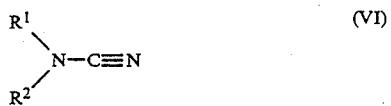

in which
R$^1$ and R$^2$ have the meanings given above, are reacted at temperatures of between 20° C. and 150° C. with chloroformic esters of the formula (VII)

Cl—COOR (VII)

in which
R represents methyl, ethyl or phenyl, preferably phenyl,
and the resulting chloroformamidine derivatives of the formula (VIII)

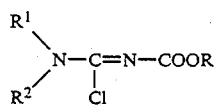

in which
R, R$^1$ and R$^2$ have the meanings given above, are reacted at temperatures of between 0° C. and 100° C., optionally after isolation by vacuum distillation or by other customary methods, with alkyl hydrazines of the formula (IX)

$$R^5-NH-NH_2 \quad (IX)$$

in which
R$^5$ has the meaning given above, optionally in the presence of diluents such as, for example, methylene chloride, dioxane and/or diethyl ether, and the product is worked up by customary methods (cf. the preparative examples).

The starting materials of the formula (III) are known organic synthesis chemicals.

The starting materials of the formula (IV) are not yet known from the literature.

The novel chlorocarbonyl-triazolinones of the formula (IV) are obtained if triazolinones of the formula (II)

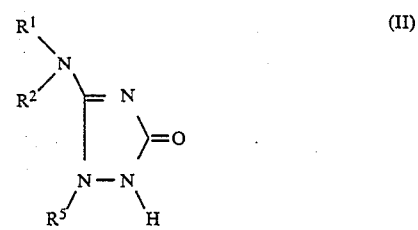

in which
R$^1$, R$^2$ and R$^5$ have the meanings given above, are reacted at temperatures of between 0° C. and 150° C. with phosgene, optionally in the presence of an acid-binder such as, for example, triethylamine, and optionally in the presence of a diluent such as, for example, toluene or acetonitrile.

The starting materials of the formula (V) are known organic synthesis chemicals.

The process (a) according to the invention for the preparation of the novel substituted triazolinones of the formula (I) is preferably carried out with the use of diluents. Suitable diluents for this purpose are virtually all inorganic solvents. These include, preferably, aliphatic and aromatic, optionally halogenated hydrocarbons, such as pentane, hexane, heptane, cyclohexane, petroleum ether, naphtha, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene, sulphone and hexamethyl phosphoric triamide.

The process (a) according to the invention can optionally be carried out in the presence of a basic reaction auxiliary. Suitable reaction auxiliaries include all the customary inorganic and organic bases. Preference is given to the use of tertiary amines such as triethylamine, N,N-dimethylaniline, pyridine, N,N-dimethylaminopyridine, diazabicyclooctane (DABCO), diazabicyclononene (DBN) or diazabicycloundecene (DBU).

However, the addition of catalysts of this type is not absolutely necessary.

The reaction temperatures for carrying out the process (a) according to the invention can be varied within wide limits. Operating temperatures of between 0° C. and +150° C., preferably temperatures of between +40° C. and +120° C. are selected.

The process (a) according to the invention is normally carried out under atmospheric pressure. However, it is also possible, in particular with gaseous starting compounds, to operate under elevated pressure.

The process (a) according to the invention is carried out using, per mole of triazolinone of the formula (II), generally 1 to 5 moles, preferably 1 to 2.5 mole of iso(-thio)cyanate of the formula (III) and optionally 1 to 2.5 mole of reaction auxiliary. Carrying out the reaction, working up and isolating the reaction products takes place analogously to generally known processes (cf. the preparative examples).

Inert organic solvents are likewise suitable as diluents for carrying out the process (b) according to the invention. Preference is given to the use of the diluents mentioned in process (a).

The process (b) according to the invention is optionally carried out in the presence of a suitable acid-binder. Suitable acid-binders include all customary inorganic or organic bases. These include, for example, alkali metal hydroxides such as sodium hydroxide or potassium hydroxide, alkali metal carbonates such as sodium carbonate, potassium carbonate or sodium hydrogen carbonate, and also tertiary amines such as triethylamine, N,N-dimethylaniline, pyridine, N,N-dimethylaminopyridine, diazabicyclooctane (DABCO), diazabicyclononene (DBN) or diazabicycloundecene (DBU).

It is also possible to use the amine of the formula (V), employed as a reactant, simultaneously in suitable excess as the acid-binder.

The reaction temperatures used for carrying out the process (b) according to the invention can be varied within wide limits. Generally, operating temperatures of between 0° C. and +150° C., preferably temperatures of between +10° C. and +80° C., are selected.

The process (b) according to the invention is normally carried out under atmospheric pressure. However, it is also possible to operate under elevated pressure.

The process (b) according to the invention is carried out using, per mole of chlorocarbonyl-triazolinone of the formula (IV), generally 1 to 5 moles, preferably 1 to 2.5 moles, of the amine of the formula (V) and optionally 1 to 2.5 moles of acid-binder. Carrying out the reaction, working up and isolating the reaction products takes place analogously to generally known processes (cf. the preparative examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panic, m, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds according to the invention of the formula (I) are also suitable, in particular, for the selective combating of dicotyledon weeds in monocotyledon crops by the preemergence and postemergence methods, in particular by the postemergence method.

Within certain limits, the compounds of the formula (I) also exhibit defoliant action in cotton, action against Pyricularia oryzae and/or also leaf insecticidal and acaricidal action.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; Furthermore also 2,4-dichlorophenoxyacetic acid (2,4-D); 4-(2,4-dichlorophenoxy)butyric acid (2,4-DB); 2,4-dichlorophenoxypropionic acid (2,4-DP); N-(methoxymethyl)-2,6-diethylchloroacetanilide (ALACHLOR); 2-chloro-4-ethylamino-6-isopropylamino-1,3,5-triazine (ATRAZINE); 3-isopropyl-2,1,3-benzothiadiazin-4-one-2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}benzenesulphonamide (CHLORSULFURON); N,N-dimethyl-N'-(3-chloro-4-methyl-phenyl)-urea (CPELaRTOLURON); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); S-ethyl N,N-di-n-propyl-thiocarbamate (EPTAME); 4-amino-6-t-butyl-3-ethyl-thio-1,2,4-triazin-5(4H)-one(ETHIOZIN); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methyl-benzoate (IMAZAMETHABENZ); 3,5-diiodo-4-hydroxybenzonitrile (IOXYNIL); N,N-dimethyl-N'-(4-isopropyl-phenyl)-urea (ISOPROTURON); (2-methyl-4-chlorophenoxy)acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2{[[((4-methoxy-6-methyl-1,3,5-triazin-2-yl)-amino)-carbonyl]-amino]-sulphonyl}-benzoic acid or its methyl ester (METSULFURON); N-(1-ethyl-propyl)-3,4-dimethyl-2,6-dinitro-aniline (PENDIMETHALIN); O-(6-chloro-3-phenyl-pyridazin-4-yl) S-octyl thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON): and N,N-diisopropyl-S-(2,3,3-trichloroallyl)-thiolcarbamate (TRIALLATE). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

Preparative Examples:

EXAMPLE 1

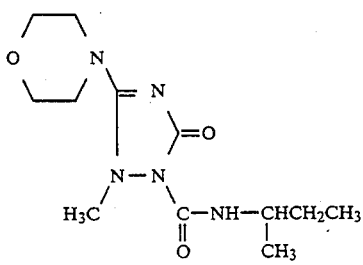

(Process (a))

2.5 g (25 pol) of sec-butyl isocyanate are added to a mixture of 4.6 g (25 mmol) of 1-methyl-5-morpholino-1,2-dihydro-3H-1,2,4-triazol-3-one and 150 ml of acetonitrile and after the addition of 2 drops of 1,8-diazabicyclo-[5.4.0]-undec-7-ene (DBU), the reaction mixture is stirred at the reflux temperature for 2 hours. After cooling, the reaction mixture is filtered off under suction and the solid product is recrystallized from hexane/ethyl acetate (1:1 by vol.).

This gives 4.4 g (62 % of theory) of 2-(sec-butyl-aminocarbonyl)-1-methyl-5-morpholino-1,2-dihydro-3H-1,2,4-triazol-3-one having a melting point of 147 ° C.

$^1$xH-NMR (CDCl$_3$, δ, ppm): 1.15–1.25; 3.35; 7.95–8.00.

EXAMPLE 2

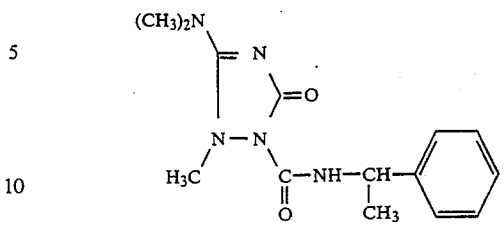

(Process (b))

To a mixture of 7.8 g (38 mmol) of 2-chlorocarbonyl-5-dimethylamino-1-methyl-1,2-dihydro-3H-1,2,4-triazol-3-one and 150 ml of acetonitrile are added dropwise with stirring 9.2 g (75 mmol) of 1-phenylethylamine so that the reaction temperature does not exceed 40° C. The reaction mixture is then stirred at 20° C. for 2 hours and then filtered. The filtrate is concentrated under water pump vacuum, the residue is shaken with methylene chloride/water and the organic phase is dried using sodium sulphate and filtered. The filtrate is freed from solvent by distillation under water pump vacuum and the solid residue is recrystallized from hexane/ethyl acetate (4:1 by vol.).

This gives 3.83 g (35 % of theory) of 5-dimethyl-amino-1-methyl-2-(1-phenyl-ethylamino-carbonyl)-1,2-dihydro-3H-1,2,4-triazol-3-one having a melting point of 103° C.

$^1$H-NMR (CDCl$_3$, δ, ppm): 1.50–1.55; 3.15; 3.30; 7.20–7.35; 8.50–8.60.

Similarly to Examples 1 and 2 and corresponding to the general discription of the preparative process according to the invention, it is also possible to prepare, for example, the compounds of the formula (I) listed in Table 1 which follows:

TABLE 1

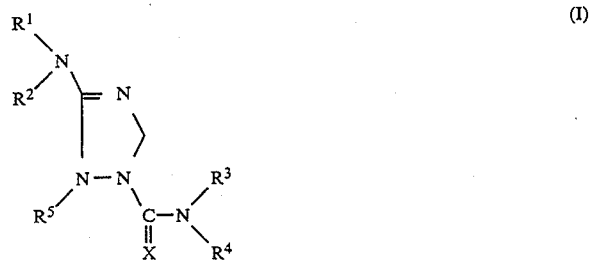

| Ex. No. | $-N\begin{smallmatrix}R^1\\R^2\end{smallmatrix}$ | $R^3$ | $R^4$ | $R^5$ | X | Melting point (°C.) or $^1$H—NMR |
|---|---|---|---|---|---|---|
| 3 | —N(CH$_3$)$_2$ | H | (3-methylphenyl) | CH$_3$ | O | 131 |
| 4 | —N(CH$_3$)$_2$ | H | —(CH$_2$)$_3$—CH$_3$ | CH$_3$ | O | $^1$H—NMR*): 0.90–0.95; 3.15;3.35 |
| 5 | —N(CH$_3$)$_2$ | H | —CH$_2$C(CH$_3$)$_3$ | CH$_3$ | O | 77 |

TABLE 1-continued (I)

$$\begin{array}{c} R^1 \\ | \\ R^2-N \\ \diagdown \\ =N \\ / \\ N-N \\ | \quad | \\ R^5 \quad C-N \\ \| \quad \diagdown \\ X \quad R^4 \end{array} \begin{array}{c} R^3 \end{array}$$

| Ex. No. | $-N\begin{array}{c}R^1\\R^2\end{array}$ | $R^3$ | $R^4$ | $R^5$ | X | Melting point (°C.) or $^1$H—NMR |
|---|---|---|---|---|---|---|
| 6 | —N(CH$_3$)$_2$ | H | 2,4-difluorophenyl | CH$_3$ | O | 207 |
| 7 | —N(C$_2$H$_5$)$_2$ | H | —CH(CH$_3$)$_2$ | CH$_3$ | O | $^1$H—NMR*): 1.20–1.25; 1.25–1.30; 3.30; 3.45–3.55; 3.95–4.05 |
| 8 | pyrrolidin-1-yl | H | —CH(CH$_3$)$_2$ | CH$_3$ | O | 133 |
| 9 | —N(CH$_3$)$_2$ | H | —C(CH$_3$)$_2$CH$_2$Cl | CH$_3$ | O | 135 |
| 10 | —N(CH$_3$)$_2$ | H | —CH(CH$_3$)CH$_2$CH$_3$ | CH$_3$ | O | $^1$H—NMR*): 1.15–1.20; 1.50–1.60; 3.15–3.35; 3.75–3.85 |
| 11 | —N(CH$_3$)$_2$ | H | —CH(CH$_3$)$_2$ | CH$_3$ | O | 63 |
| 12 | —N(CH$_3$)$_2$ | H | cyclohexyl | CH$_3$ | O | 82 |
| 13 | N(CH$_3$)$_2$ | H | —(CH$_3$)$_2$CH$_2$F | CH$_3$ | O | 110 |
| 14 | —N(CH$_3$)$_2$ | H | —(CH$_3$)$_3$ | CH$_3$ | O | 135 |
| 15 | —N(CH$_3$)$_2$ | H | phenyl | CH$_3$ | O | 158 |
| 16 | —N(C$_2$H$_5$)$_2$ | H | —C(CH$_3$)$_3$ | CH$_3$ | O | 108 |
| 17 | —N(C$_2$H$_5$)$_2$ | H | —C(CH$_3$)$_2$CH$_2$Cl | CH$_3$ | O | 82 |
| 18 | —N(CH$_3$)$_2$ | H | 1-methylcyclohexyl | CH$_3$ | O | 140 |
| 19 | —N(CH$_3$)$_2$ | H | —CH$_2$CH=CH$_2$ | CH$_3$ | O | $^1$H—NMR*): 3.15; 3.35; 3.90–3.95; 5.70–5.95; 8.25–8.30 |
| 20 | —N(CH$_3$)$_2$ | H | —CH$_2$CH$_2$CH$_3$ | CH$_3$ | O | $^1$H—NMR*): |

TABLE 1-continued $$\text{(I)}$$

Structure: R¹R²N-C(=N-)-N(R⁵)-N-C(=X)-NR³R⁴ (cyclic triazine-like with pendant groups)

| Ex. No. | -NR¹R² | R³ | R⁴ | R⁵ | X | Melting point (°C.) or ¹H—NMR |
|---|---|---|---|---|---|---|
| | | | | | | 0.90–1.00; 1.55–1.65; 3.15; 3.35 |
| 21 | —N(CH₃)₂ | H | C₂H₅ | CH₃ | O | 81 |
| 22 | —N(CH₃)₂ | H | —CH(C₂H₅)₂ | CH₃ | O | ¹H—NMR*): 0.90–1.00; 1.40–1.65; 3.15; 3.35 |
| 23 | —N(CH₃)₂ | H | —CH₂CH₂Cl | CH₃ | O | ¹H—NMR*): 3.15; 3.35; 3.65 |
| 24 | —N(CH₃)₂ | H | —CHCH(CH₃)₂<br>    \|<br>   CH₃ | CH₃ | O | ¹H—NMR*): 0.90–0.95; 1.15–1.20; 1.70–1.85; 3.15; 3.35 |
| 25 | —N(CH₃)₂ | H | 1-methylcyclopentyl | CH₃ | O | 127 |
| 26 | —N(C₂H₅)₂ | H | cyclohexyl | CH₃ | O | 105 |
| 27 | —N(C₂H₅)₂ | H | phenyl | CH₃ | O | 107 |
| 28 | —N(CH₃)₂ | H | —C(CH₂Cl)₂<br>    \|<br>   CH₃ | CH₃ | O | 99 |
| 29 | —N(CH₃)₂ | H | —C(CH₃)₂CHCl₂ | CH₃ | O | 93 |
| 30 | —N(CH₃)₂ | H | 2-chlorophenyl | CH₃ | O | 109 |
| 31 | —N(CH₃)₂ | H | 4-chlorophenyl | CH₃ | O | 172 |
| 32 | —N(CH₃)₂ | H | 4-methylcyclohexyl | CH₃ | O | 143 |

TABLE 1-continued
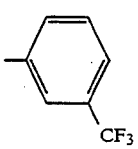
(I)
| Ex. No. | $-N\begin{smallmatrix}R^1\\R^2\end{smallmatrix}$ | $R^3$ | $R^4$ | $R^5$ | X | Melting point (°C.) or $^1$H—NMR |
|---|---|---|---|---|---|---|
| 33 | —N(CH$_3$)$_2$ | H | 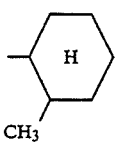 | CH$_3$ | O | 177 |
| 34 | —N(CH$_3$)$_2$ | H | 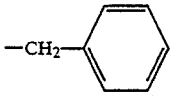 | CH$_3$ | O | 109 |
| 35 | —N(CH$_3$)$_2$ | H | —CH$_2$—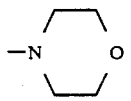 | CH$_3$ | O | 76 |
| 36 | 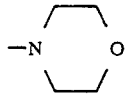 | H | —C(CH$_3$)$_3$ | CH$_3$ | O | 148 |
| 37 | 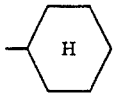 | H | 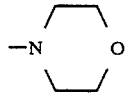 | CH$_3$ | O | 165 |
| 38 | 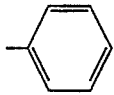 | H | 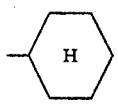 | CH$_3$ | O | 225 |
| 39 | —N[CH(CH$_3$)$_2$]$_2$ | H | —CHCH$_2$CH$_3$<br>\|<br>CH$_3$ | CH$_3$ | O | 124 |
| 40 | —N[CH(CH$_3$)$_2$]$_2$ | H | —C(CH$_3$)$_3$ | CH$_3$ | O | 140 |
| 41 | —N[CH(CH$_3$)$_2$]$_2$ | H | 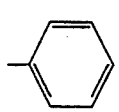 | CH$_3$ | O | 166 |
| 42 | —N[CH(CH$_3$)$_2$]$_2$ | H |  | CH$_3$ | O | 172 |

TABLE 1-continued

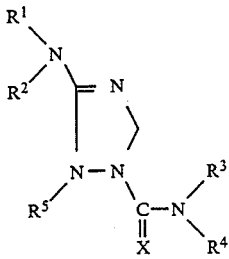

| Ex. No. | $-N\begin{matrix}R^1\\R^2\end{matrix}$ | $R^3$ | $R^4$ | $R^5$ | X | Melting point (°C.) or $^1H$—NMR |
|---|---|---|---|---|---|---|
| 43 | —N(morpholine) | CH₃ | CH₃ | CH₃ | O | 138 |
| 44 | —N(pyrrolidine) | H | phenyl | CH₃ | O | 191 |
| 45 | —N(piperidine) | H | phenyl | CH₃ | O | 177 |
| 46 | —N(piperidine) | H | —C(CH₃)₃ | CH₃ | O | 121 |
| 47 | —N(pyrrolidine) | H | —CHCH₂CH₃<br>   \|<br>  CH₃ | CH₃ | O | $^1H$—NMR*):<br>0.90–0.95;<br>1.18–1.22;<br>3.35;<br>3.60–3.65 |
| 48 | —N(piperidine) | H | —CHCH₂CH₃<br>   \|<br>  CH₃ | CH₃ | O | $^1H$—NMR*):<br>1.18–1.22;<br>1.15–1.20;<br>3.20;<br>3.55–3.60;<br>3.75–3.90 |
| 49 | —N(piperidine) | H | —CH(CH₃)₂ | CH₃ | O | 112 |
| 50 | —N(piperidine) | H | cyclohexyl | CH₃ | O | 120 |
| 51 | —N(CH₃)(C₂H₅) | H | cyclohexyl | CH₃ | O | 84 |

TABLE 1-continued (I)

| Ex. No. | -N(R¹)(R²) | R³ | R⁴ | R⁵ | X | Melting point (°C.) or ¹H—NMR |
|---|---|---|---|---|---|---|
| 52 | -N(CH₃)(C₂H₅) | H | -C(CH₃)₃ | CH₃ | O | 83 |
| 53 | -N(CH₃)(C₂H₅) | H | phenyl | CH₃ | O | 126 |
| 54 | -N(CH₃)(C₂H₅) | H | -CH(CH₃)₂ | CH₃ | O | ¹H—NMR*): 1.20–1.23; 1.25–1.30; 3.1; 3.3; 3.50–3.60; 3.95–4.05 |
| 55 | -N(CH₃)(C₂H₅) | H | -C(CH₃)₂CH₂F | CH₃ | O | 77 |
| 56 | -N(CH₃)₂ | H | -C(CH₃)₂C≡CH | CH₃ | O | 163 |
| 57 | -N(CH₃)(C₂H₅) | H | -CH(CH₃)CH₂CH₃ | CH₃ | O | ¹H—NMR*): 1.18–1.22; 1.26–1.30; 1.50–1.60; 3.15; 3.35 |
| 58 | -N(CH₃)₂ | H | cyclopropyl | CH₃ | O | 115 |
| 59 | -N(CH₃)₂ | H | 4-SCF₃-phenyl | CH₃ | O | |
| 60 | -N(CH₃)₂ | H | -CH₂-cyclohexyl | CH₃ | O | ¹H—NMR*): 0.90–1.80; 3.15; 3.35 |
| 61 | morpholino | H | 4-OCF₃-phenyl | CH₃ | O | 183 |
| 62 | -N[CH(CH₃)₂]₂ | H | 4-SCF₃-phenyl | CH₃ | O | 192 |

TABLE 1-continued $$\text{(I)}$$

Structure (I): R¹R²N-C(=N-...)-... triazole ring with N-R⁵ and N-C(=X)-NR³R⁴ substituents.

| Ex. No. | -N(R¹)(R²) | R³ | R⁴ | R⁵ | X | Melting point (°C.) or $^1$H—NMR |
|---|---|---|---|---|---|---|
| 63 | piperidin-1-yl | H | 4-(SCF₃)-C₆H₄ | CH₃ | O | 192 |
| 64 | pyrrolidin-1-yl | H | 4-(SCF₃)-C₆H₄ | CH₃ | O | 182 |
| 65 | morpholin-4-yl | H | 4-CH₃-cyclohexyl | CH₃ | O | 169 |
| 66 | morpholin-4-yl | H | 3-CH₃-cyclohexyl | CH₃ | O | 150 |
| 67 | morpholin-4-yl | H | 2-CH₃-cyclohexyl | CH₃ | O | 159 |
| 68 | —N(CH₃)₂ | H | CH₃ | CH₃ | S | 103 |
| 69 | —N(CH₃)(C₂H₅) | H | CH₃ | CH₃ | S | (amorphous) |
| 70 | —N(CH₃)(C₂H₅) | H | C₂H₅ | CH₃ | S | 83 |
| 71 | pyrrolidin-1-yl | H | —C(CH₃)₃ | CH₃ | O | 132 |

TABLE 1-continued
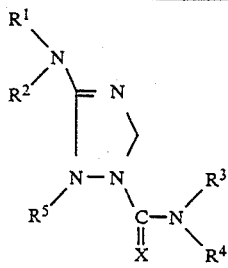
(I)
| Ex. No. | —N(R¹)(R²) | R³ | R⁴ | R⁵ | X | Melting point (°C.) or $^1$H—NMR |
|---|---|---|---|---|---|---|
| 72 | 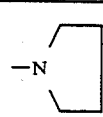 | H | 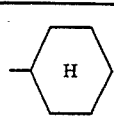 | CH₃ | O | 94 |
| 73 | 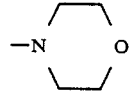 | H | —CH(CH₃)₂ | CH₃ | O | 172 |
| 74 | 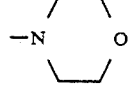 | H | —C(CH₃)₂CH₂F | CH₃ | O | 159 |
| 75 | 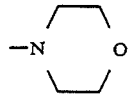 | H | —CH₂C(CH₃)₃ | CH₃ | O | 152 |
| 76 | 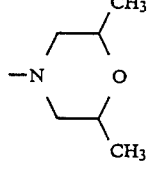 | H | 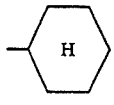 | CH₃ | O | 132 |
| 77 | —N(CH₃)₂ | H | 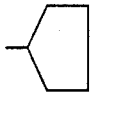 | CH₃ | O | 62 |
| 78 | 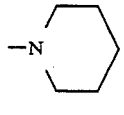 | H | 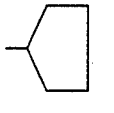 | CH₃ | O | 99 |
| 79 | 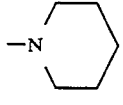 | H | 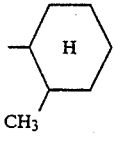 | CH₃ | O | 125 |
| 80 | 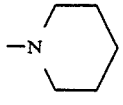 | CH₃ | CH₃ | CH₃ | O | 130 |

TABLE 1-continued
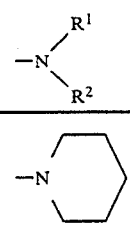
(I)
| Ex. No. | -N(R¹)(R²) | R³ | R⁴ | R⁵ | X | Melting point (°C.) or ¹H—NMR |
|---|---|---|---|---|---|---|
| 81 | 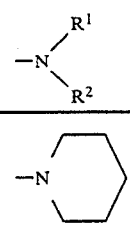 | H | 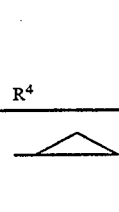 | CH₃ | S | 136 |
| 82 | 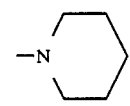 | H | CH₃ | CH₃ | S | 114 |
| 83 | 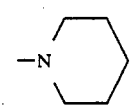 | H | —CH(C₂H₅)₂ | CH₃ | O | (amorphous) |
| 84 | 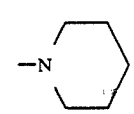 | H | —CH(CH₃)CH(CH₃)₂ | CH₃ | O | (amorphous) |
| 85 | 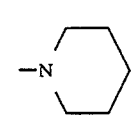 | H | —CH₂C(CH₃)₃ | CH₃ | O | (amorphous) |
| 86 | 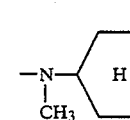 | H | 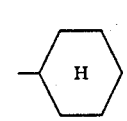 | CH₃ | O | 117 |
| 87 | 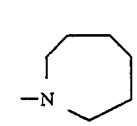 | H | 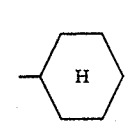 | CH₃ | O | 113 |
| 88 | 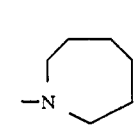 | H | —CH(CH₃)₂ | CH₃ | O | 88 |
| 89 | 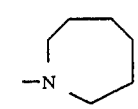 | H | —CH(CH₃)CH₂CH₃ | CH₃ | O | (amorphous) |
| 90 | —N(CH₃)₂ | H | —CH₂CH(CH₃)₂ | CH₃ | O | (amorphous) |

TABLE 1-continued $$\text{(I)}$$

| Ex. No. | $-N\genfrac{}{}{0pt}{}{R^1}{R^2}$ | $R^3$ | $R^4$ | $R^5$ | X | Melting point (°C.) or $^1$H—NMR |
|---|---|---|---|---|---|---|
| 91 | -N(morpholine with 2,6-diCH₃) | H | —CH(CH₃)₂ | CH₃ | O | $^1$H—NMR*): 1.15–1.25; 3.35; 3.95–4.05 |
| 92 | —N(CH₃)₂ | H | 1-ethylcyclopentyl (C₂H₅) | CH₃ | O | $^1$H—NMR*): 0.85–0.90; 1.80–1.90; 1.55–1.80; 3.15; 3.35 |
| 93 | —N(CH₃)₂ | H | —CH(CH₃)CH₂OCH₃ | CH₃ | O | $^1$H—NMR*): 1.20–1.25; 3.15; 3.35; 4.05–4.15 |
| 94 | —N(piperidine) | H | —CH(CH₃)CH₂OCH₃ | CH₃ | O | $^1$H—NMR*): 1.20–1.25; 3.30; 3.35–3.40; 4.05–4.15 |
| 95 | —N(CH₃)₂ | H | cyclohexyl | —CH(CH₃)₂ | O | 118° C. |
| 96 | —N(CH₃)₂ | H | —CH(CH₃)₂ | —CH(CH₃)₂ | O | 83° C. |
| 97 | —N(CH₃)(C₂H₅) | H | (S)—CH(CH₃)—cyclohexyl | CH₃ | O | $^1$H—NMR*): 1.14–1.17; 3.10; 3.32; 3.70–3.82; 8.05–8.10 |
| 98 | —N(CH₃)(C₂H₅) | H | 4-methylcyclohexyl | CH₃ | O | 97° C. |
| 99 | —N(CH₃)(C₂H₅) | H | —CH₂—phenyl | CH₃ | O | 97° C. |

TABLE 1-continued $$\text{(I)}$$

| Ex. No. | -N(R¹)(R²) | R³ | R⁴ | R⁵ | X | Melting point (°C.) or ¹H—NMR |
|---|---|---|---|---|---|---|
| 100 | -N(CH₃)(C₂H₅) | H | 4-methylcyclohexyl | CH₃ | O | ¹H—NMR*): 0.90–0.92; 3.10; 3.30 3.55–3.63; |
| 101 | -N(CH₃)(C₂H₅) | H | 2-methylcyclohexyl | CH₃ | O | ¹H—NMR*): 0.90–0.96; 3.10; 3.30 3.50–3.56; |
| 102 | -N(CH₃)(C₂H₅) | H | cyclopentyl | CH₃ | O | 54° C. |
| 103 | -N(CH₃)(C₂H₅) | H | —CH(CH₃)—CH₂—O—CH₃ | CH₃ | O | ¹H—NMR*): 1.20–1.30; 3.10; 3.32 3.37; 3.49–3.56 |
| 104 | -N(CH₃)(C₂H₅) | H | —CH(CH₃)—CH(CH₃)₂ | CH₃ | O | ¹H—NMR*): 0.90–0.95; 1.14–1.16 1.25–1.30; 3.50–3.55 |
| 105 | -N(CH₃)(C₂H₅) | H | —CH₂—C(CH₃)₃ | CH₃ | O | ¹H—NMR*) 0.95; 1.25–1.30; 3.12; 3.32; 3.50–3.60 |
| 106 | -N(CH₃)(C₂H₅) | H | —CH₂—CH₂—CH₃ | CH₃ | O | ¹H—NMR*) 0.92–0.98; 3.12; 3.32 3.50–3.60 |
| 107 | -N(CH₃)(C₂H₅) | H | —CH(CH₃)—CH₂—CH₃ | CH₃ | O | ¹H—NMR*): 1.25–1.30; 1.32–1.35 3.05–3.10; 3.60–3.65 |
| 108 | -N(CH₃)(C₂H₅) | H | —CH(CH₃)—C(CH₃)₃ | CH₃ | O | ¹H—NMR*): 0.95; 1.12–1.15; 1.25–1.30; 3.12; 3.32; 3.70–3.80 |

TABLE 1-continued (I)

[Structure: general formula with R¹, R² on amidine nitrogen, ring system with R⁵ on N, C(=X)NR³R⁴]

| Ex. No. | -N(R¹)(R²) | R³ | R⁴ | R⁵ | X | Melting point (°C.) or $^1$H—NMR |
|---|---|---|---|---|---|---|
| 109 | -N(CH₃)(C₂H₅) | H | -(CH₂)₃-CH₃ | CH₃ | O | $^1$H—NMR*): 0.90-0.96; 1.33-1.60; 3.12; 3.25-3.30; 3.32 |
| 110 | -N(CH₃)(C₂H₅) | H | -CH₂-C₆H₁₁ | CH₃ | O | $^1$H—NMR*) 1.25-1.30; 3.12; 3.13-3.15; 3.32; 3.50-3.56 |
| 111 | -N(CH₃)₂ | H | -CH(CH₃)-C(CH₃)₃ | CH₃ | O | 115° C. |
| 112 | -N(CH₃)₂ | H | -CH(CH₃)C₂H₅ | CH(CH₃)₂ | O | 50° C. |
| 113 | -N(CH₃)₂ | H | -C₆H₁₁ | CH(CH₃)₂ | O | 118° C. |
| 114 | -N(CH₃)₂ | H | -CH(CH₃)₂ | CH(CH₃)₂ | O | 83° C. |
| 115 | -N(CH₃)₂ | H | -C(CH₃)₂CH₂Cl | CH(CH₃)₂ | O | 81° C. |
| 116 | -N(CH₃)₂ | H | -CH(CH₃)-C₂H₅ | -C₆H₁₁ | O | 86° C. |
| 117 | -N(CH₃)₂ | H | -CH₂-CH(CH₃)₂ | C₂H₅ | O | $^1$H—NMR*) 0.95-0.98; 0.99-1.05; 1.78-1.90; 3.12-3.15; 3.18; 3.85-3.92 |
| 118 | -N(CH₃)₂ | H | -C₆H₁₁ | C₂H₅ | O | $^1$H—NMR*) 0.90-1.05; 1.18-1.22; 1.50-1.60; 3.18; 3.80-3.90 |
| 119 | -N(CH₃)₂ | H | -CH(CH₃)C₂H₅ | C₂H₅ | O | (amorphous) |
| 120 | -N(CH₃)₂ | H | -CH(CH₃)₂ | C₂H₅ | O | 52° C. |

TABLE 1-continued

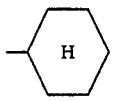

| Ex. No. | -N(R¹)(R²) | R³ | R⁴ | R⁵ | X | Melting point (°C.) or ¹H—NMR |
|---|---|---|---|---|---|---|
| 121 | —N(CH$_3$)$_2$ | H | —C$_6$H$_{11}$ | —C$_6$H$_{11}$ | O | 123° C. |
| 122 | —N(CH$_3$)$_2$ | H | —CH(CH$_3$)$_2$ | —C$_6$H$_{11}$ | O | 115° C. |
| 123 | —N(CH$_3$)(C$_2$H$_5$) | H | —CH(CH$_3$)—C$_2$H$_5$ | CH(CH$_3$)$_2$ | O | ¹H—NMR*): 3.12; 3.50–3.60; 3.75–3.85; 7.85–7.90 |
| 124 | —N(CH$_3$)(C$_2$H$_5$) | H | —CH(CH$_3$)$_2$ | CH(CH$_3$)$_2$ | O | ¹H—NMR*): 1.20–1.25; 3.12; 3.50–3.60; 3.75–3.85; 3.95–4.05; 7.89–7.92 |
| 125 | —N(CH$_3$)(CH(CH$_3$)$_2$) | H | —C$_6$H$_{11}$ | CH$_3$ | O | 75° C. |
| 126 | —N(CH$_3$)(CH$_2$CH$_2$CH$_3$) | H | —C$_6$H$_{11}$ | CH$_3$ | O | ¹H—NMR*): 3.15; 3.30 3.40–3.50; 3.60–3.75; |
| 127 | —N(CH$_3$)(CH(CH$_3$)$_2$) | H | —CH—(CH$_3$)$_2$ | CH$_3$ | O | 155° C. |
| 128 | —N(CH$_3$)(CH$_2$CH$_2$CH$_3$) | H | —CH(CH$_3$)—C$_2$H$_5$ | CH$_3$ | O | ¹H—NMR*): 1.40–1.45; 3.12; 3.30 3.40–3.50; 3.75–3.90 |
| 129 | —N(CH$_3$)(CH$_2$CH$_2$CH$_3$) | H | —CH(CH$_3$)$_2$ | CH$_3$ | O | 62° C. |

TABLE 1-continued $$\text{(I)}$$

Structure: R¹R²N-C(=N-...)-N(R⁵)-N-C(=X)-N(R³)(R⁴) (triazinone ring)

| Ex. No. | -N(R¹)(R²) | R³ | R⁴ | R⁵ | X | Melting point (°C.) or ¹H—NMR |
|---|---|---|---|---|---|---|
| 130 | -N(CH₃)(CH(CH₃)₂) | H | -CH(CH₃)-C₂H₅ | CH₃ | O | 63° C. |
| 131 | -N(morpholino) | H | -CH(CH₃)-C₂H₅ | C₂H₅ | O | 72° C. |
| 132 | -N(CH₃)₂ | H | -CH₂CH(CH₃)₂ | cyclohexyl | O | ¹H—NMR*): 0.90–0.95; 1.10–1.90; 3.08–3.12; 3.15 |
| 133 | -N(CH₃)₂ | H | 4-(SCF₃)-C₆H₄- | cyclohexyl | O | 115° C. |
| 134 | -N(morpholino) | H | 4-CH₃-cyclohexyl | C₂H₅ | O | 108° C. |
| 135 | -N(CH₃)(CH₂CH₂CH₃) | H | -CH₂C(CH₃)₃ | CH₃ | O | (amorphous) |
| 136 | -N(CH₃)(CH₂CH₂CH₃) | H | -CH(C₂H₅)₂ | CH₃ | O | (amorphous) |
| 137 | -N(CH₃)(CH₂CH₂CH₃) | H | -CH(CH₃)CH(CH₃)₂ | CH₃ | O | 100° C. |
| 138 | -N(CH₃)(CH(CH₃)₂) | H | -CH₂C(CH₃)₃ | CH₃ | O | (amorphous) |
| 139 | -N(CH₃)(CH(CH₃)₂) | H | -CH(C₂H₅)₂ | CH₃ | O | 95° C. |

TABLE 1-continued

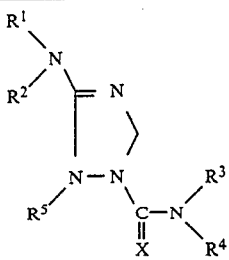

(I)

| Ex. No. | -N(R¹)(R²) | R³ | R⁴ | R⁵ | X | Melting point (°C.) or ¹H—NMR |
|---|---|---|---|---|---|---|
| 140 | -N(CH₃)(CH(CH₃)₂) | H | -CH(CH₃)CH(CH₃)₂ | CH₃ | O | 85° C. |
| 141 | morpholino (-N(CH₂CH₂)₂O) | H | cyclohexyl | CH(CH₃)₂ | O | 125° C. |
| 142 | -N(CH₃)(CH₂CH₂CH₃) | H | 4-methylcyclohexyl | CH₃ | O | (amorphous) |
| 143 | -N(CH₃)(C₆H₁₃-n) | H | cyclohexyl | CH₃ | O | (amorphous) |
| 144 | -N(CH₃)(CH₂CH₂CN) | H | cyclohexyl | CH₃ | O | (amorphous) |
| 145 | -N(CH₃)(C₆H₁₃-n) | H | -CH(CH₃)C₂H₅ | CH₃ | O | (amorphous) |
| 146 | -N(CH₃)(CH₂CH(OCH₃)₂) | H | cyclohexyl | CH₃ | O | (amorphous) |
| 147 | -N(CH₃)(CH₂CH(OCH₃)₂) | H | -CH(CH₃)C₂H₅ | CH₃ | O | (amorphous) |
| 148 | -N(CH₃)(CH₂CH(OCH₃)₂) | H | -CH(CH₃)₂ | CH₃ | O | (amorphous) |
| 149 | -N(CH₃)(CH(CH₃)₂) | H | 4-methylcyclohexyl | CH₃ | O | (amorphous) |

TABLE 1-continued $$\text{(I)}$$

Structure (I): a triazole-like core with substituents $R^1, R^2$ on one nitrogen (via amidine), $R^5$ on ring nitrogen, and a C(=X)N($R^3$)($R^4$) group.

| Ex. No. | $-N\begin{smallmatrix}R^1\\R^2\end{smallmatrix}$ | $R^3$ | $R^4$ | $R^5$ | X | Melting point (°C.) or $^1$H—NMR |
|---|---|---|---|---|---|---|
| 150 | $-N(CH_3)(C_4H_9\text{-}n)$ | H | 3-methylcyclohexyl (H) | $CH_3$ | O | (amorphous) |
| 151 | $-N(CH_3)(C_4H_9\text{-}n)$ | H | 4-methylcyclohexyl (H) | $CH_3$ | O | (amorphous) |
| 152 | $-N(CH_3)(C_4H_9\text{-}n)$ | H | cyclohexyl (H) | $CH_3$ | O | (amorphous) |
| 153 | 3-methylcyclohexyl (H) | H | cyclohexyl (H) | $CH_3$ | O | 116° C. |
| 154 | $-N(CH_3)(C_4H_9\text{-}n)$ | H | $-CH(CH_3)C_2H_5$ | $CH_3$ | O | (amorphous) |
| 155 | $-N(CH_3)(C_4H_9\text{-}n)$ | H | $-CH(CH_3)_2$ | $CH_3$ | O | (amorphous) |
| 156 | $-N(CH_3)(C_4H_9\text{-}n)$ | H | $-CH(CH_3)CH(CH_3)_2$ | $CH_3$ | O | (amorphous) |
| 157 | 3-methylcyclohexyl (H) | H | 3-methylcyclohexyl (H) | $CH_3$ | O | (amorphous) |
| 158 | 3-methylcyclohexyl (H) | H | $-CH(CH_3)CH(CH_3)_2$ | $CH_3$ | O | (amorphous) |

TABLE 1-continued

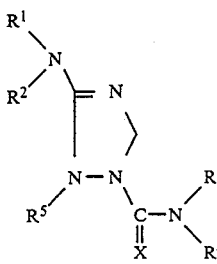

(I)

| Ex. No. | -N(R¹)(R²) | R³ | R⁴ | R⁵ | X | Melting point (°C.) or ¹H—NMR |
|---|---|---|---|---|---|---|
| 159 | 4-methylcyclohexyl (H) | H | —CH(CH₃)₂ | CH₃ | O | 80° C. |
| 160 | 3-methylcyclohexyl (H) | H | —CH(C₂H₅)₂ | CH₃ | O | (amorphous) |
| 161 | 3-methylcyclohexyl (H) | H | —CH(CH₃)C₂H₅ | CH₃ | O | (amorphous) |
| 162 | —N(C₂H₅)(C₄H₉-n) | H | —CH(C₂H₅)₂ | CH₃ | O | (amorphous) |
| 163 | —N(CH₃)(C₄H₉-n) | H | —CH₂C(CH₃)₃ | CH₃ | O | (amorphous) |
| 164 | 3-methylcyclohexyl (H) | H | —CH₂C(CH₃)₃ | CH₃ | O | (amorphous) |
| 165 | —N(CH₃)(CH(CH₃)C(CH₃)₃) | H | —CH(CH₃)C₂H₅ | CH₃ | O | (amorphous) |
| 166 | —N(CH₃)(CH(CH₃)C(CH₃)₃) | H | cyclohexyl (H) | CH₃ | O | (amorphous) |

TABLE 1-continued $$\text{(I)}$$

| Ex. No. | $-N\begin{matrix}R^1\\R^2\end{matrix}$ | $R^3$ | $R^4$ | $R^5$ | X | Melting point (°C.) or $^1H$—NMR |
|---|---|---|---|---|---|---|
| 167 | $-N\begin{matrix}CH_3\\CHC(CH_3)_3\\ \vert \\CH_3\end{matrix}$ | H | $-CH_2C(CH_3)_3$ | $CH_3$ | O | (amorphous) |
| 168 | $-N\begin{matrix}CH_3\\CH_2-C_6H_5\end{matrix}$ | H | $-CH_2CH(CH_3)_2$ | $CH_3$ | O | (amorphous) |
| 169 | $-N\begin{matrix}CH_3\\CH_2-C_6H_5\end{matrix}$ | H | $-\underset{\underset{CH_3}{\vert}}{CH}C_2H_5$ | $CH_3$ | O | 72° C. |
| 170 | $-N\begin{matrix}CH_3\\CH_2-C_6H_5\end{matrix}$ | H | cyclohexyl | $CH_3$ | O | 101° C. |
| 171 | $-N\begin{matrix}CH_3\\CH_2-C_6H_5\end{matrix}$ | H | $-CH_2C(CH_3)$ | $CH_3$ | O | 106° C. |
| 172 | $-N\begin{matrix}CH_3\\CH_2-C_6H_5\end{matrix}$ | H | $-CH(CH_3)_2$ | $CH_3$ | O | 87° C. |
| 173 | $-N\begin{matrix}CH_3\\CH_2-C_6H_5\end{matrix}$ | H | cyclopentyl | $CH_3$ | O | 103° C. |
| 174 | $-N\begin{matrix}\\O\end{matrix}$ (morpholino) | H | $-\underset{\underset{CH_3}{\vert}}{\overset{\overset{CH_3}{\vert}}{C}}-CH_2CH_2-C_6H_5$ | $CH_3$ | O | 93° C. |
| 175 | $-N\begin{matrix}\\O\end{matrix}$ (morpholino) | H | $-\underset{\underset{CH_3}{\vert}}{CH}-C_6H_5$ [S(−)] | $CH_3$ | O | (amorphous) |

TABLE 1-continued $$\begin{array}{c} R^1 \\ | \\ R^2-N \\ \diagdown \\ C=N \\ | \\ N-N \\ R^5 \diagup \quad \diagdown C-N \diagup R^3 \\ \| \quad \diagdown R^4 \\ X \end{array} \quad (I)$$

| Ex. No. | $-N\begin{smallmatrix}R^1\\R^2\end{smallmatrix}$ | $R^3$ | $R^4$ | $R^5$ | X | Melting point (°C.) or $^1$H—NMR |
|---|---|---|---|---|---|---|
| 176 | —N(morpholino) | H | —CH(CH$_3$)—C$_6$H$_5$ [R(+)] | CH$_3$ | O | (amorphous) |
| 177 | —N(morpholino) | H | —CH$_2$—C$_6$H$_5$ | CH$_3$ | O | 149° C. |
| 178 | —N(CH$_3$)(CH$_2$C$_6$H$_5$) | H | —C(CH$_3$)$_2$—CH$_2$CH$_2$—C$_6$H$_5$ | CH$_3$ | O | (amorphous) |
| 179 | —N(CH$_3$)(CH$_2$CH$_2$CN) | H | —CH$_2$CH(CH$_3$)$_2$ | CH$_3$ | O | (amorphous) |
| 180 | —N(CH$_3$)(CH$_2$CH$_2$CN) | H | —CH(C$_2$H$_5$)CH$_3$ | CH$_3$ | O | (amorphous) |

*)The $^1$N—NMR spectra were recorded from solutions in CDCl$_3$ using tetramethylsilane (TMS) as internal standard. The chemical shift is given by the δ value in ppm.

Starting materials of the formula (II):

EXAMPLE (II-1)

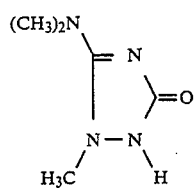

1st step:

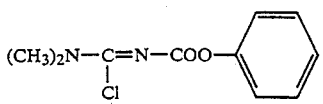

A mixture of 35 g (0.5 mol) of dimethylcyanamide and 156 g (1.0 mol) of phenyl chloroformate is stirred for 16 hours at 100° C. Then the more readily volatile components are distilled off under water pump vacuum (bath temperature 80° C.) and the oily residue is distilled under oil pump vacuum.

This gives 61.4 g (54% of theory) of N,N-di-methyl-N'-phenoxycarbonyl-chloroformamidine having a boiling range of 158° C.–165° C./0.5 mbar–0.8 mbar.

2nd step:

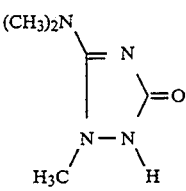

A solution of 6.9 g (0.15 mol) of methylhydrazine in 100 ml of dioxane is added dropwise with stirring at 20° C. to 30° C. (cooling necessary!) to a mixture of 17.0 g (0.075 mol) of N,N-dimethyl-N'-phenoxycarbonyl-chloroformamidine and 100 ml of methylene chloride. The reaction mixture is stirred for 4 hours at 20° C. and then filtered off under suction. The filtrate is freed of solvent by distillation under water pump vacuum and the liberated phenol is distilled off under oil pump vacuum.

This gives 9.8 g (92 % of theory) of 5-dimethylamino-1-methyl-1,2-dihydro-3H-1,2,4-triazol-3-one in the form of an oily residue.

$^1$H-NMR (DMSO-d6, δ, ppm): 3.20; 3.45.

The product can be crystallized by boiling with acetonitrile; melting point 222° C.

EXAMPLE (II-2)

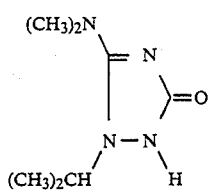

1st step:

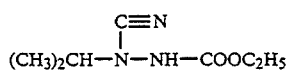

73 g (0.5 mol) of ethyl 2-isopropylhydrazinecarboxylate and 42 g (0.5 mol) of sodium hydrogencarbonate are introduced into 200 ml of methylene chloride and 400 ml of water. 55 g (0.52 mol) of bromocyanogen are introduced with stirring at room temperature (cooling necessary). After subsequent stirring for three hours, the evolution of $CO_2$ has ceased. The organic phase is separated off in a separating funnel, dried over sodium sulphate and concentrated in a rotary evaporator.

This gives a residue of 73 g (85.4 % of theory) of ethyl 2-isopropyl-2-cyanohydrazinecarboxylate in the form of a light oil.

$^1$H-NMR: (CDCl$_3$, δ, ppm): 1.25–1.30; 1.30–1.35; 3.5–3.65; 4.20–4.30.

2nd step:

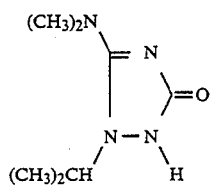

To a solution of 100 ml of 33% strength dimethylamine in absolute ethanol are added dropwise 35 g (0.2 mol) of ethyl 2-isopropyl-2-cyano-hydrazinecarboxylate. The solution is first stirred for 8 hours at room temperature and then for 1.5 hours at the reflux temperature. Concentration in a rotary evaporator gives an oily residue which slowly crystallizes on standing. Recrystallization from cyclohexane/ethyl acetate (4:1 by vol.) gives 30 g (88% of theory) of 5-dimethylamino-1-isopropyl-1,2-dihydro-3H-1,2,4-triazol-3-one having a melting point of 111° C.

A similar method can be used, for example, to prepare the compounds of the formula (II) listed in Table 2 which follows:

TABLE 2

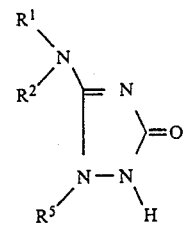

Examples of the starting materials of the formula (II)

| Ex. No. | R$^1$ | R$^2$ | R$^5$ | Melting point (°C.) |
|---|---|---|---|---|
| II-3 | C$_2$H$_5$ | C$_2$H$_5$ | CH$_3$ | 89 |
| II-4 | —CH$_2$CH$_2$—O—CH$_2$CH$_2$— | | CH$_3$ | 183 |
| II-5 | —(CH$_2$)$_4$— | | CH$_3$ | (amorph) |
| II-6 | —(CH$_2$)$_5$— | | CH$_3$ | (amorph) |
| II-7 | CH(CH$_3$)$_2$ | CH(CH$_3$)$_2$ | CH$_3$ | 119 |
| II-8 | CH$_3$ | C$_2$H$_5$ | CH$_3$ | (amorph) |
| II-9 | CH$_3$ | CH$_3$ | C$_2$H$_5$ | |

Starting materials of the formula (IV):

EXAMPLE (IV-1)

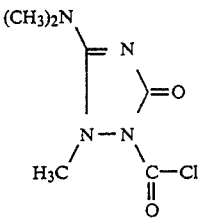

A mixture of 14.2 g (0.1 mol) of 5-dimethylamino-1-methyl-1,2-dihydro-3H-1,2,4-triazol-3-one and 200 ml of acetonitrile is heated at the reflux temperature while introducing phosgene and phosgenated until hydrogen chloride evolution has ceased. Subsequently nitrogen is blown through the mixture and the solvent is then carefully distilled off under water pump vacuum.

This gives 18.5 g (91% of theory) of 2-chlorocarbonyl-5-dimethylamino-1-methyl-1,2-dihydro-3H-1,2,4-triazol-3-one in the form of an oily residue which is used without further purification or characterization for the next step according to process (b).

Application Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, excellent herbicidal activity is shown by, for example, the compounds according to Preparative Examples 1, 5, 7, 9, 10, 11, 12, 13, 14, 16, 20, 21, 22, 23, 24, 25, 32, 34, 49 and 54.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0% = no action (like untreated control)

100% = total destruction

Excellent herbicidal activity and good to very good productive plant selectivity are shown in this test by, for example, the compounds according to Preparative Examples 1, 2, 4, 5, 9, 10, 11, 12, 13, 14, 20, 21, 22, 23, 24, 25, 26, 28, 29, 32, 34, 35 and 36.

It will be appreciated that the instant specification is set forth by way of illustration and not limitation, and that various modifications and changes may be made without departing from the spirit and scope of the present invention.

What is claimed is:

1. A substituted triazolinone of the formula

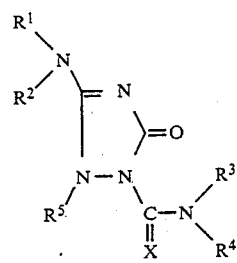

in which
R¹ and R², together with the nitrogen atom to which they are bonded, represent a pyrrolidino, piperidino, morpholino or azacycloheptanyl radical, each of which may be mono-, di- or tri-substituted by identical or different substituents selected from the group consisting of halogen, alkyl and halogenoalkyl, wherein the alkyl moieties in said substituents each have from 1 to 4 carbon atoms,
R³ represents hydrogen,
R⁴ represents methyl, ethyl, n- or i-propyl, n-, i-, s- or t-butyl, allyl, propargyl, pentyl, hexyl, heptyl, butenyl, pentenyl, butynyl, pentynyl or hexynyl each of which is straight-chain or branched, halogenoalkyl having 1 to 5 carbon atoms and 1 to 9 identical or different halogen atoms, cyclopropyl, cyclopentyl or cylohexyl each of which is optionally mono-, di- or tri-substituted by identical or different substituents from the group consisting of methyl, ethyl, fluorine and chlorine, represents phenyl, benzyl or phenylethyl each of which is optionally mono-, di- or tri-substituted by identical or different substituents selected from the group consisting of fluorine, chlorine, methyl, ethyl, methoxy, ethoxy, methylthio, trifluoromethyl, trifluoromethylthio, benzyl and phenylethyl,
R⁵ represents methyl, ethyl, n- or i-propyl, and
X represents oxygen.

2. The compound 2-(sec-butyl-aminocarbonyl)-1-methyl 5-morpholino-1,2-dihydro-3H-1,2,4-triazol-3-one of the formula

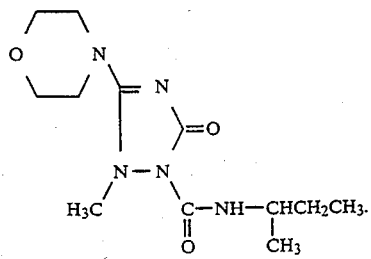

3. A method of combating unwanted vegetation which comprises applying to such vegetation or to a locus from which it is desired to exclude such vegetation a herbicidally effective amount of a compound selected from the group consisting of
2- (sec-butyl-aminocarbonyl) 1-1-methyl 5-morpholino-1,2-dihydro-3H-1,2,4-triazol-3-one.

* * * * *

UNITED STATES PATENT AND TRADEMARK OFFICE
CERTIFICATE OF CORRECTION

PATENT NO. : 5,441,924
DATED : August 15, 1995
INVENTOR(S) : Findeisen, et al.

It is certified that error appears in the above-indentified patent and that said Letters Patent is hereby corrected as shown below:

Title Page    [30]  Foreign Application Priority Data:
              Delete " Dec. 9, 1989 " and substitute
              -- Dec. 2, 1989 --

Signed and Sealed this

Twelfth Day of December, 1995

Attest:

BRUCE LEHMAN

Attesting Officer

Commissioner of Patents and Trademarks